United States Patent
Bancroft et al.

(10) Patent No.: US 10,390,515 B2
(45) Date of Patent: Aug. 27, 2019

(54) BOLUS ANTENNA SYSTEM

(71) Applicant: Phase IV Engineering, Inc., Boulder, CO (US)

(72) Inventors: Randy Cecil Bancroft, Denver, CO (US); Scott David Dalgleish, Boulder, CO (US)

(73) Assignee: Herdstrong LLC, Greeley, CO (US)

( * ) Notice: Subject to any disclaimer, the term of this patent is extended or adjusted under 35 U.S.C. 154(b) by 0 days.

(21) Appl. No.: 15/965,641

(22) Filed: Apr. 27, 2018

(65) Prior Publication Data

US 2018/0310522 A1      Nov. 1, 2018

Related U.S. Application Data

(60) Provisional application No. 62/491,358, filed on Apr. 28, 2017.

(51) Int. Cl.
*A61B 5/00* (2006.01)
*A61B 5/07* (2006.01)
(Continued)

(52) U.S. Cl.
CPC .......... *A01K 11/007* (2013.01); *A61B 5/0008* (2013.01); *A61B 5/01* (2013.01); *A61B 5/073* (2013.01); *H01Q 1/2208* (2013.01); *H01Q 1/273* (2013.01); *H01Q 9/26* (2013.01); *H01Q 21/0075* (2013.01); *H01Q 21/06* (2013.01); *H01Q 21/29* (2013.01); *A61B 5/1118* (2013.01); *A61B 5/1123* (2013.01); *A61B 2503/40* (2013.01); *A61B 2560/0214* (2013.01); *A61B 2562/0219* (2013.01); *H01Q 1/42* (2013.01)

(58) Field of Classification Search
CPC ....... A61B 5/01; A61B 5/0205; A61B 5/0024; A61B 5/02055; A61B 1/041; A61B 5/0002; A61B 5/0028; A61B 5/0031; A61B 5/07; A61B 5/073; A61B 5/076; A01K 11/004; A01K 11/006; A01K 11/008; A01K 29/005; A01K 1/03; A01K 1/031; G01W 1/08; H01Q 1/273
USPC .................. 600/301, 302; 340/573.3, 870.1; 343/718
See application file for complete search history.

(56) References Cited

U.S. PATENT DOCUMENTS

5,482,008 A   1/1996  Stafford et al.
6,012,415 A   11/2000 Linseth
(Continued)

*Primary Examiner* — Binh B Tran
(74) *Attorney, Agent, or Firm* — Kenneth Altshuler (57) ABSTRACT

A bolus that communicates with an external transceiver by way of radio waves produced by an electrically small H-antenna is described. The electrically small H-antenna is connected to a conductive cylindrical antenna that houses a battery and chipset that includes a transceiver, identification information and at least one sensor. The H-antenna and the conductive cylindrical antenna are arranged so that electrical currents that produce the radio waves are essentially always aligned to work together. The bolus is essentially a hermetically sealed capsule containing the antennas that is meant to be ingested by a cow or other ruminant animal. The bolus is configured to transmit radio waves in essentially an omnidirectional pattern more efficiently when the boluses inside of a cow stomach than when the boluses outside of the cow.

20 Claims, 10 Drawing Sheets

(51) Int. Cl.
*A01K 11/00* (2006.01)
*H01Q 9/26* (2006.01)
*H01Q 21/00* (2006.01)
*H01Q 21/06* (2006.01)
*H01Q 1/27* (2006.01)
*H01Q 1/22* (2006.01)
*H01Q 21/29* (2006.01)
*A61B 5/01* (2006.01)
*H01Q 1/12* (2006.01)
*H01Q 1/42* (2006.01)
*A61B 5/11* (2006.01)

(56) References Cited

U.S. PATENT DOCUMENTS

| | | |
|---|---|---|
| 6,371,927 B1 | 4/2002 | Brune et al. |
| 7,026,939 B2 | 4/2006 | Letkomiller et al. |
| 7,112,752 B1 | 9/2006 | Wenner |
| 7,558,620 B2 | 7/2009 | Ishibashi |
| 8,640,712 B2 | 2/2014 | Ardrey |
| 8,771,201 B2 | 7/2014 | Gabriel et al. |
| 9,504,231 B2 | 11/2016 | Rosenkranz et al. |
| 2002/0010390 A1 | 1/2002 | Guice et al. |
| 2006/0132317 A1 | 6/2006 | Letkomiller et al. |
| 2007/0088194 A1 | 4/2007 | Tahar et al. |
| 2008/0236500 A1 | 10/2008 | Hodges et al. |
| 2009/0105557 A1 | 4/2009 | Najafi et al. |
| 2009/0187392 A1 | 7/2009 | Riskey et al. |
| 2009/0228074 A1* | 9/2009 | Edgell ............ A61N 1/37229 607/60 |
| 2010/0300462 A1 | 12/2010 | Ardrey |
| 2012/0161964 A1 | 6/2012 | Rettedal et al. |
| 2012/0265272 A1* | 10/2012 | Judkins ............ A61N 1/37223 607/60 |
| 2012/0277550 A1 | 11/2012 | Rosenkranz et al. |
| 2016/0360994 A1 | 12/2016 | Rettedal et al. |

* cited by examiner

BOLUS ANTENNA SYSTEM

CROSS-REFERENCE TO RELATED APPLICATIONS

This application is a non-provisional application which claims priority to and the benefit of U.S. Provisional Patent Application Ser. No. 62/491,358, entitled BOLUS ANTENNA SYSTEM filed Apr. 28, 2017, the entire disclosure of which is hereby incorporated by reference.

FIELD OF THE INVENTION

The present embodiments are directed to two-way radio frequency communication between an implantable bolus device residing in an animal and a receiver that is external to the animal.

DESCRIPTION OF RELATED ART

For at least three decades, ranchers have been monitoring their cattle by way of ID systems transmitted from boluses ingested by each of their cattle. Generally speaking, ruminant animals, such as a cow, can be administered a bolus capsule that encase electronic identification systems and sensors, such as temperature sensors. Upon swallowing a bolus, a cow or bull will typically retain the bolus permanently in their second stomach compartment or reticulum. In general, a bolus includes a battery, and other electronics that wirelessly broadcast identification numbers and sensor values. In some instances, boluses do not have a battery but rather rely on power through inductive fields commonly used in passive RFID systems. Nevertheless, if a bolus is going to transmit data wirelessly it is going to require an antenna. Because the ruminant animal that hosts the bolus inherently attenuates signals transmitted by the bolus, engineers and designers use antennas that have a number of loops to approximate the wavelength of the frequency transmitted by the bolus. Moreover, engineers and designers use lower frequencies around or below 300 MHz transmitted to better travel through the animal. Because transmission is typically relegated to a few feet away, the ruminant animal sometimes wears an amplifier system on their ear or around their neck to extend the signal to a receiver. Those designs that do not employ an amplifier on the external part of the animal, depend on directional transmission from the bolus. By directionally transmitting signals, a bolus can transmit 50 to 75 feet in one direction.

It is to innovations related to this subject matter that the claimed invention is generally directed.

SUMMARY OF THE INVENTION

The present invention is directed to one-way and two-way near omnidirectional radio frequency communication between an implantable bolus residing in an animal and a receiver or receivers that are external to the animal.

Certain embodiments of the present invention contemplate a bolus comprising an electrically small H-antenna extending from a front side of a ground plate, the H-antenna electrically connected to a power supply and a signal transmitter by way of a microstrip transmission line, the microstrip transmission line opposing a ground plane that is at least three times greater width than the microstrip transmission line and separated from the microstrip transmission line by a dielectric spacer, the H-antenna comprising two parallel dipoles and two parallel plate transmission lines; a conductive cylindrical antenna extending from a backside of the ground plate and electrically connected to the ground plate, the metal cylindrical antenna essentially housing the power supply; the bolus configured to radiate essentially omnidirectional electromagnetic waves generated by electrical currents aligned and in a common direction in both the parallel dipoles and the conductive cylindrical antenna when powered by the signal transmitter.

Other embodiments contemplate the bolus just described further comprising a capsule that encapsulates and hermetically seals the electrically small H-antenna, the signal transmitter, the ground plate, the dielectric spacer, the microstrip, a battery, and the conductive cylindrical antenna. Certain embodiments envision the bolus being weighted to stay retained in a stomach of a ruminant animal throughout the life of the ruminant animal. Other embodiments contemplate the two parallel plate transmission lines possess opposite electrical currents that cancel each other out when the signal transmitter provides power to the antenna. Some embodiments envision the omnidirectional electromagnetic waves are significantly attenuated when the bolus is in operation outside of a ruminant animal compared to being in the ruminant animal. This can be accomplished with the signal transmitter which can be comprised by a printed circuit board that possesses static circuits that tune the H-antenna to transmit the electromagnetic waves at a significantly higher efficiency when the bolus is inside of the ruminant animal as compared to outside of the ruminant animal. Yet other embodiments contemplate the bolus further comprising a printed circuit board that is shielded from the electrical currents by the conductive cylindrical antenna. The dipoles of the H-antenna in some embodiments are spaced apart approximately the same distance as the diameter of the metal cylindrical antenna. The bolus is envisioned in some constructs to be configured for two-way communication using radio frequency with an external transceiver. Certain elements of the bolus can include a unique identification and at least one sensor adapted to measure a physical parameter associated with a host ruminant animal, the unique identification and at least one value associated with the physical parameter adapted to be transmitted by the omnidirectional magnetic waves.

Yet, other embodiments of the present invention can therefore comprise a bolus comprising: an electrically small H-antenna extending from a conductive cylindrical antenna; a ground plate interposed between the H-antenna and the conductive cylindrical antenna and electrically connected to the H-antenna and the conductive cylindrical antenna; a battery disposed inside of the conductive cylindrical antenna; and a signal transmitter configured to generate electrical currents that essentially align in one direction in both the H-antenna and the conductive cylindrical antenna, the H-antenna and the conductive cylindrical antenna are adapted to generate radiofrequency waves from the electrical currents. Certain embodiments envision the bolus being weighted to remain inside of a ruminant animal's stomach until the ruminant animal is no longer living. The bolus can comprise a unique identification and at least one sensor adapted to measure a physical parameter associated with a host ruminant animal, the unique identification and at least one value associated with the physical parameter adapted to be transmitted by the radiofrequency waves. In certain embodiments, the radiofrequency waves are essentially omnidirectional. Other embodiments of the present invention contemplate the bolus possessing circuitry that is configured to tune at least the H-antenna to transmit the radiofrequency waves more efficiently when the bolus is disposed in a ruminant animal than when the bolus is located outside of the ruminant animal.

Yet further embodiments of the present invention contemplate a method comprising: providing a bolus possessing an electrically small H-antenna and a conductive cylindrical antenna, the H-antenna possessing two parallel dipoles that are in line with the outer surface of the conductive cylindrical antenna; energizing the H-antenna and the conductive cylindrical antenna with a battery contained in the conductive cylindrical antenna via a signal transmitter to generate electrical currents that are essentially pointed in the same direction along the dipoles and the outer surface of the conductive cylindrical antenna; transmitting at least identification of the bolus via a radio signal wave generated by the electrical currents in the dipoles and the outer surface of the conductive cylindrical antenna. The antennas are envisioned in some constructions to further comprising alternating the electrical currents at a frequency over 800 MHz. It is further envisioned that the method could additionally comprise generating essentially omnidirectional radio waves via the H-antenna and the conductive cylindrical antenna. In some ideas, the radio wave transmitted by the bolus is significantly more attenuated by the antenna when the bolus is transmitting signals outside of a ruminant animal than when the bolus is transmitting signals inside of the ruminant animal. Some embodiments contemplate obtaining at least one sensor value from a sensor within the bolus and transmitting the at least one sensor value via the radio signal wave to an external receiving device.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving similar uses of electrically small antennas. In what follows, similar or identical structures may be identified using identical callouts.

Aspects of the present invention are generally related to two-way radiofrequency (RF) communication between an implantable bolus residing in an animal and a receiver that is external to the animal. For ease of explanation, embodiments described herein are directed to a bolus retained in a cow, and more specifically in a cow's stomach. However, the described embodiments are not limited to a bolus, nor is there any limitation to use in a cow or other ruminant animal, which include cattle, sheep, deer, goats, giraffes, etc. Nonetheless, the bolus embodiments can be advantageously used in a ruminant animal to monitor the ruminant animal's whereabouts and bodily functions, for example. In the case of a herd of cows, each cow can be monitored to determine if they are in a certain part of a field, are in a barn or corral, are sick or healthy, etc. In the case of a cow, a bolus is inserted down the cow's throat using a bolus applicator whereby the bolus passes into the cow's stomach. Typically, a bolus settles into the cow's reticulum. Regardless, the bolus is weighted so that it does not progress through the cow's digestive system through the cow's intestines and out the back end of the cow, or back up the throat of the cow and into the cow's mouth. The bolus is weighted to essentially sit inside of the cow's gut for the remainder, or length, of the cow's life.

Certain embodiments described herein are directed to a bolus capable of two-way wireless communication whereby the bolus can possess one or more sensors to monitor an animal's a) physical condition/internal vital signs, b) location, c) activity level (walking, running, lying down, eating, drinking, reticulo-rumen activity to identify changes in reticulum/rumen activity levels, etc.), d) identity, or other characteristics of interest about the animal. An omnidirectional radio frequency antenna, from the family of electrically small antennas, is disposed inside of the bolus along with the appropriate transceiver, memory, power supply (e.g., battery), RFID, bio sensors, computer processor and related computer functional capabilities. One or more external transceivers can be used to communicate with the bolus when in range of the bolus. Information gathered (and potentially processed onboard the bolus to identify illness, treatment, drug recommendations, etc., maybe even stored in history) by the one or more external transceivers can be transmitted to a computer system where the information can be gathered and stored, manipulated, reported upon, transmitted elsewhere, etc. Certain embodiments envision multiple external transceivers spaced apart such that the transceivers are essentially usually but not always in range of an animal occupying a particular region, such as pens or a pasture.

Certain embodiments contemplate an electrically small H-antenna connected to a conductive cylindrical antenna that houses a battery and chipset. The chipset can include, among other things, a transceiver, identification information uniquely tied to the bolus, processor and at least one sensor. The H-antenna and the conductive cylindrical antenna are arranged so that electrical currents that produce the radio waves are essentially always aligned to work together. The bolus is essentially a hermetically sealed capsule containing the antennas, which is intended to be ingested by a cow or other ruminant animal. The bolus is configured to transmit radio waves in essentially an omnidirectional pattern more efficiently when the bolus is inside of a cow stomach than when the bolus is outside of the cow (in air, for example).

Figure 1A:
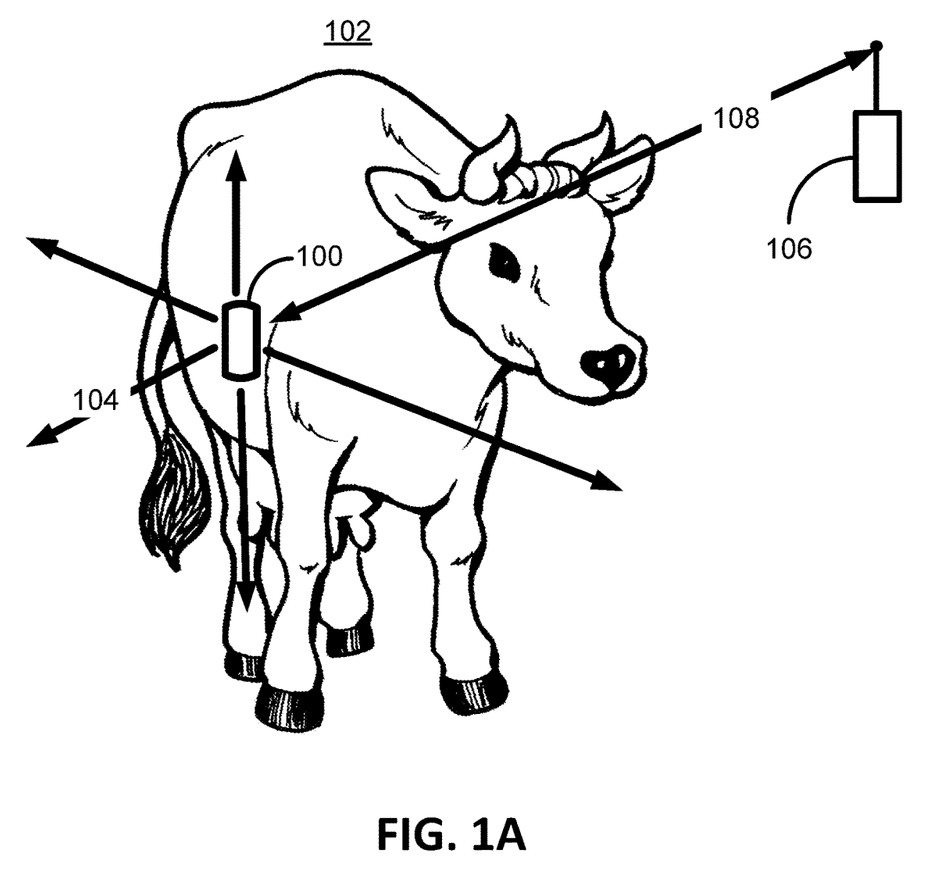
FIG. 1A illustratively depicts a bolus ingested by a cow transmitting radio wave signals in an omnidirectional pattern consistent with embodiments of the present invention.

Referring to FIG. 1A, a cow 102 is illustratively shown with an ingested bolus 100 transmitting data about the cow 102 by way of radio waves 104 in essentially an omnidirectional pattern as illustratively shown by the arrows. The bolus 100 is approximately 3 to 4½ inches in length and 1 inch in diameter and could vary in size according to the particular animal application. In this figure, the bolus transmissions are picked up by the external transceiver 106 whereby two-way communication can occur between the external transceiver 106 and the bolus 100, depicted by the two-way arrow 108.

Figure 1B:
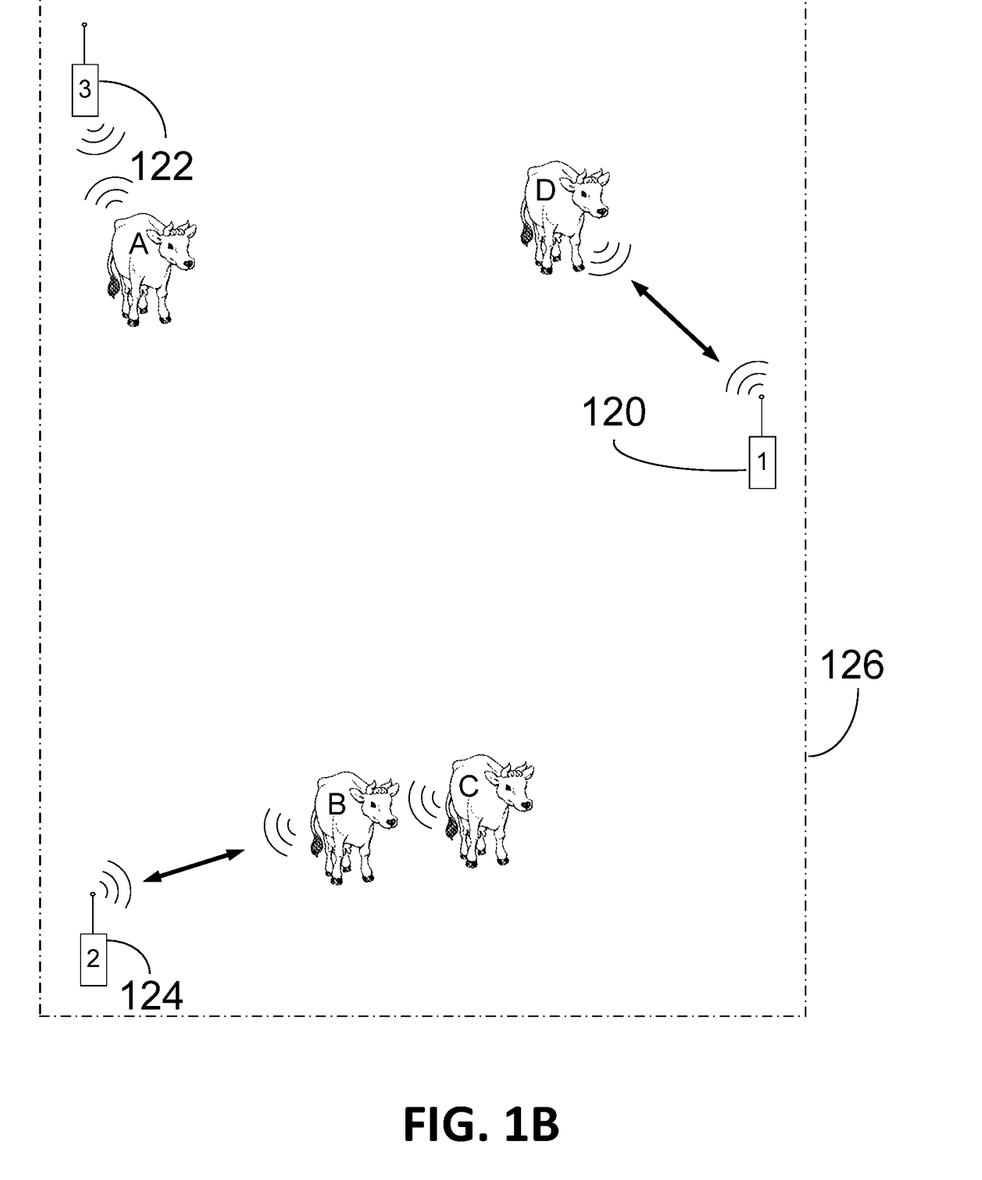
FIG. 1B illustratively shows a plurality of cows distributed in a fenced in region transmitting radio wave signals in an omnidirectional pattern to external transceiver devices consistent with embodiments of the present invention.

FIG. 1B illustratively shows a plurality of cows distributed in a fenced in region 126. Here, cows A-D each have an implanted bolus that specifically identifies each animal. For example, cow "A" is identified by bolus "A", cow "B" is identified by bolus "B", and so on. In this embodiment, there are three external transceivers 120-124 spaced apart and distributed in the fenced region 126. Accordingly, cow "D" is in two-way communication with external transceiver #1 120, cow "A" is in two-way communication with external transceiver #3 122, and cows "B" and "C" are in two-way communication with external transceiver #2 124. The cows can be in constant communication with the external transceivers, in intermittent communication with the external transceivers at set periods of time, or when contacted by an external transceiver, just to name three examples of how two-way communication is initiated. Of course, intermittent communication techniques will help preserve battery life of the bolus 100 by placing the bolus 100 into a quiescent state (or sleep state), discussed in more detail later. This can be accomplished with the appropriate circuitry internal to the bolus 100, or optionally can be controlled by an external transceiver 106. In the embodiment where the external transceiver 106 controls a quiescent state of a bolus, the external transceiver 106 instructs the bolus 100 to go into a quiescent state and then after a set amount of time or at the discretion of an operator the external transceiver 106 (or different external transceiver) can instruct the bolus 100 to wake up and be fully operational. In other embodiments, the external transceiver 106 can send updated "transmit interval times" to the bolus 100, which in turn causes the bolus 100 to utilize those updated times to control the sleep mode. Certain embodiments envision a battery that can provide constant power to the bolus 100 throughout the life of the host cow 102. Certain embodiments contemplate a bolus 100 associated with a particular host cow taking vital signs (in addition to other sensed information) and then storing those vital signs in the bolus memory with the appropriate time stamp (time/day/order/etc.) followed by transmitting the data associated with a particular bolus/cow to an external transceiver 106. In some cases, after being transmitted, there may be no need to retain the data inside of the bolus memory, hence the data can be erased. Erasure can occur immediately after transmission or at some designated time thereafter. Certain embodiments contemplate transmitting data from one external transceiver to another before going to a host computer (not shown), e.g., information from external transceiver-3 122 passing data to external transceiver-2 124, whereby external transceiver-2 124 sends all data in possession to a host computer. Optionally, a high reliability over the air radio transmit methodology can be employed, which can include a clear channel assessment (cca) to verify that there is no other bolus or external transceiver transmitting before a bolus starts to send data over the radio. An external transceiver can be equipped with a real-time clock that may be used to reset all bolus clocks in RF range. Some embodiments envision that a given bolus 100 will go into a "receive" mode after transmitting and attempt to receive a message back from an external transceiver 106 with an acknowledgment, updated time, or other bolus reconfiguration message/s.

Figure 2:
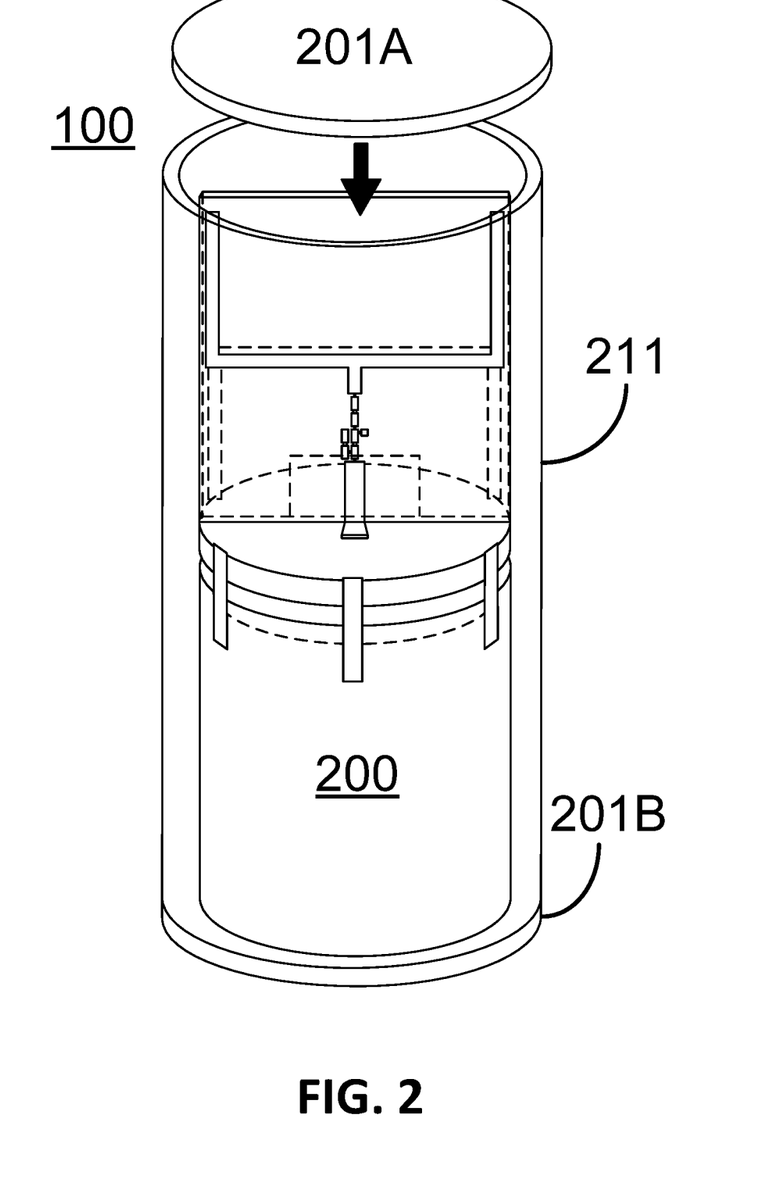
FIG. 2 depicts an embodiment of certain basic internal elements of a bolus consistent with embodiments of the present invention.

The weighted bolus 100 is essentially a "smart" capsule incorporated with internal electrical components. FIG. 2 depicts an embodiment of certain basic internal elements of the bolus 100 consistent with embodiments of the present invention. In the embodiment shown, the bolus 100 generally comprises a nonmetallic bolus case tube 211, which in one embodiment is a polymer, having a pair of end caps 201A and 201B that hermetically seal the bolus internal components 200 from the contents of a cow's stomach. Certain embodiments envision one endcap, while the other end is simply molded with the capsule like a test tube. The interface between the end caps 201A and 201B and bolus case tube 211 can be sealed/welded by way of an adhesive, for example, ultrasonic welding, or other means known to those skilled in the art.

Figure 3:
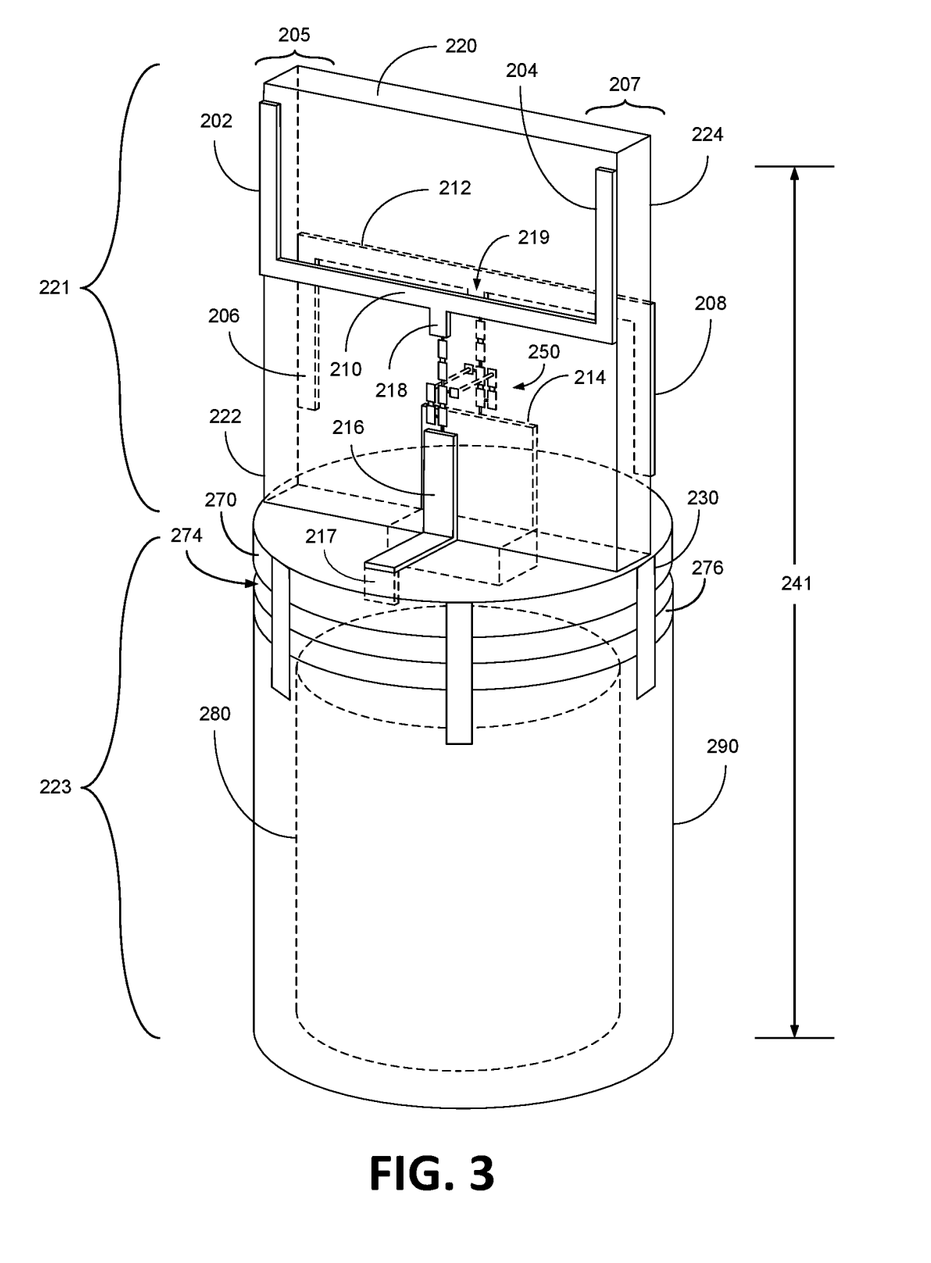
FIG. 3 illustratively depicts a more detailed perspective of an embodiment of the bolus internal components consistent with embodiments of the present invention.

FIG. 3 illustratively depicts an embodiment of the bolus internal components 200 consistent with embodiments of the present invention. For ease of explanation, the bolus internal components 200 will hereafter be shortened to simply the "bolus 200" when believed appropriate. In operation, the bolus 200 functions as a single antenna. On the upper part of the bolus 200 is an H-antenna 221 and the lower part of the bolus 200 is a conductive (metal) cylindrical antenna 223.

In greater physical detail, the present embodiment of FIG. 3 depicts the H-antenna portion 221 possessing a dielectric spacer 220, that is a clear polymer in this drawing, that has a front side 222 and the backside 224. The dielectric spacer 220 is about 1.5 mm thick that serves as a dielectric separating the microstrip transmission line 216 and the microstrip transmission line's ground plane 214. Certain embodiments contemplate the H-antenna portion 221 being constructed from standard printed circuit board materials and techniques. There is a first parallel plate transmission line 210 on the front side 222 of the spacer 220 whereby a first radiator 202 extends at 90° in an upward direction from one end of the first parallel plate transmission line 210 and a second radiator 204 extends at 90° in an upward direction from the other end of the first parallel plate transmission line 210. In the center of the first parallel plate transmission line 210 extending downward is a first parallel plate transmission line feed 218. Electrically connected to a printed circuit board 276 is a microstrip transmission line 216 at a driving point 217. Between the microstrip transmission line 216 and the first parallel plate transmission lead line 218 is a lattice balun (balanced to unbalanced) circuit 250 comprising lumped inductors and capacitors. On the backside 224 of the dielectric spacer 220 is a second parallel plate transmission line 212 whereby a third radiator 206 extends at 90° in a downward direction from one end of the second parallel plate transmission line 212 and the fourth radiator 208 that extends at 90° in a downward direction from the other end of the second parallel plate transmission line 212. In the center of the second parallel plate transmission line 212 extending downward is a second parallel plate transmission line feed 219. The other portion of the lattice balun circuit 250 connects to a microstrip transmission line ground plane 214.

Certain embodiments contemplate adding potting material (not shown) around the H-antenna 221 to add weight to the overall bolus 100. Moreover, the potting material can be somewhat rigid to stabilize the H-antenna 221 inside of the bolus 100. Potting material can be designed with an appropriate dielectric constant using various fillers, or optionally passive components for the antenna structure 221 can be used to match the dielectric constant of the potting material to improve RF transmission.

The H-antenna portion 221 is an electrically small antenna generally comprised of a pair of dipole antenna elements 205 and 207 that are directly fed with a parallel plate transmission lines 210 and 212 at a central driving point 218 and 219. Parallel plate transmission lines 210 and 212 are inherently electrically balanced as arranged. Electrically small antennas are defined as having a maximum dimension that is less than $\lambda/2\pi$ (as defined by Wheeler in 1947). In this embodiment, each dipole is about 24 mm long (see FIG. 6) and the RF wavelength ($\lambda$) is about 325 mm. The dipoles 205 and 207 are electrically close (i.e., so close together compared with the RF wavelength that the dipoles 205 and 207 behave like a single dipole and not as an array. That is, the dipoles 205 and 207 are spaced apart about 10% of the wavelength transmitted by the dipoles 205 and 207). The pair of dipoles 205 and 207 add to the stability of the H-antenna 221. The first dipole 205 is essentially comprised of the first radiator 202 and the third radiator 206, and the second dipole 207 is essentially comprised of the second radiator 204 and the fourth radiator 208.

Figure 4A:
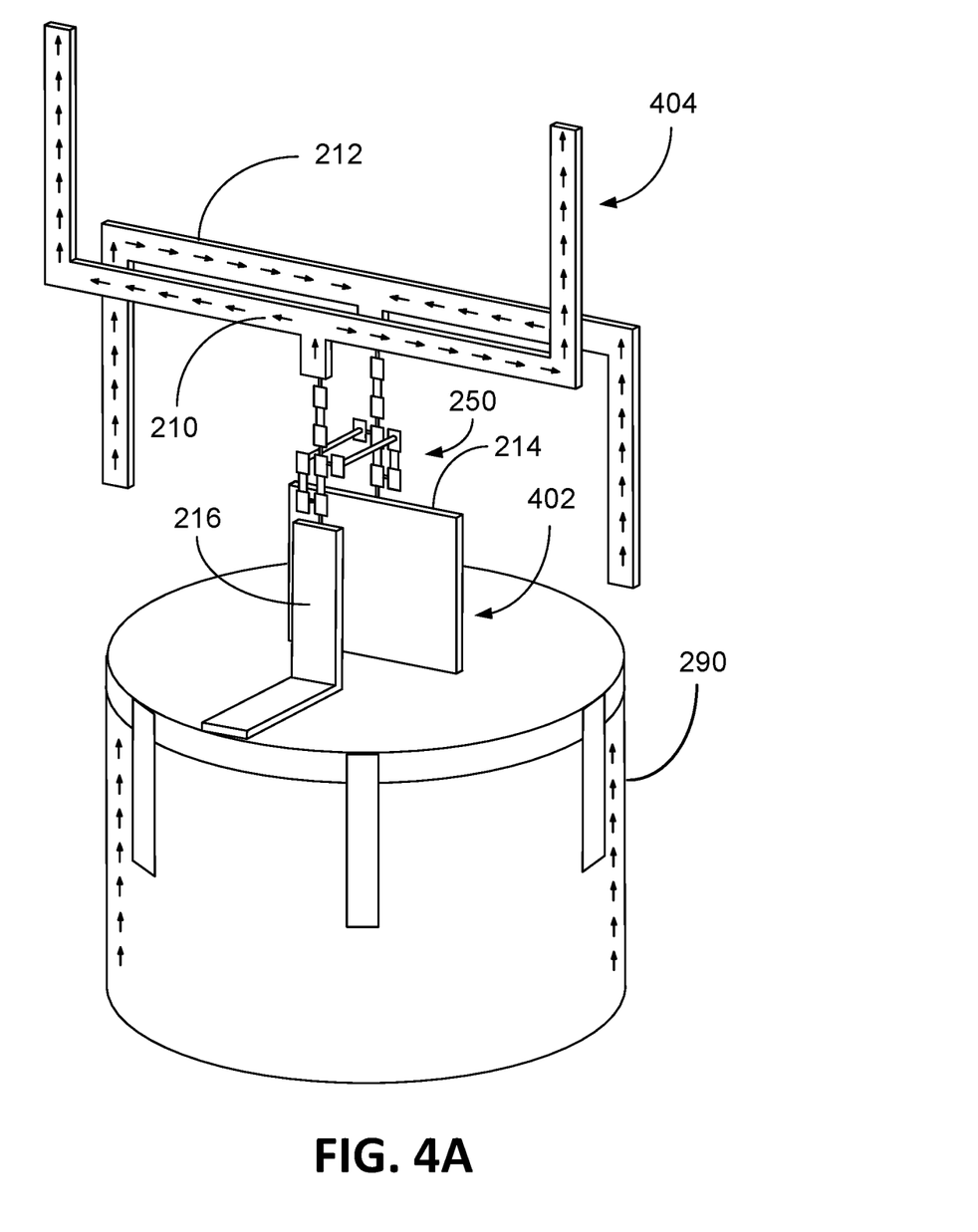
FIG. 4A depicts one state of electrical currents generated in the bolus antenna consistent with embodiments of the present invention.

One state (as opposed to the alternating current states required to generate electromagnetic waves) of the electrical currents is depicted by arrows as shown in FIG. 4A. The dipole pair 205 and 207 electrically couples to the conductive cylindrical element 290, thus making the cylindrical element 290 part of the overall radiating antenna. This enforces the omnidirectional electromagnetic wave radiating pattern shown in FIG. 4B. The H-antenna 221 has a driving point impedance with a large reactive value. This reactive part of the impedance is canceled with a pair of lumped elements forming the balun circuit 250. This cancellation creates a driving point impedance that is pure real at the design frequency. Because the driving point of most integrated circuits is designed to accept an unbalanced impedance, the lattice balun 250 comprised of lumped elements is integrated to both change the resistive value to that required by the PCB 276 and to act as a balun to change the transmission line mode from unbalanced to balanced. The microstrip transmission line 216 connects parallel plate transmission lines 210 and 212 of the H-antenna 221 to the radiofrequency PCB 276. There is a 0° and 180° phase difference of the currents generated in the first parallel plate transmission line 210 and the second parallel plate transmission line 212, which causes the currents to cancel out, and therefore produces a virtual ground between them. In other words, the opposite currents essentially cancel out in the first and second parallel plate transmission lines 210 and 212, therefore avoiding inadvertent feedline radiation.

Figure 6:
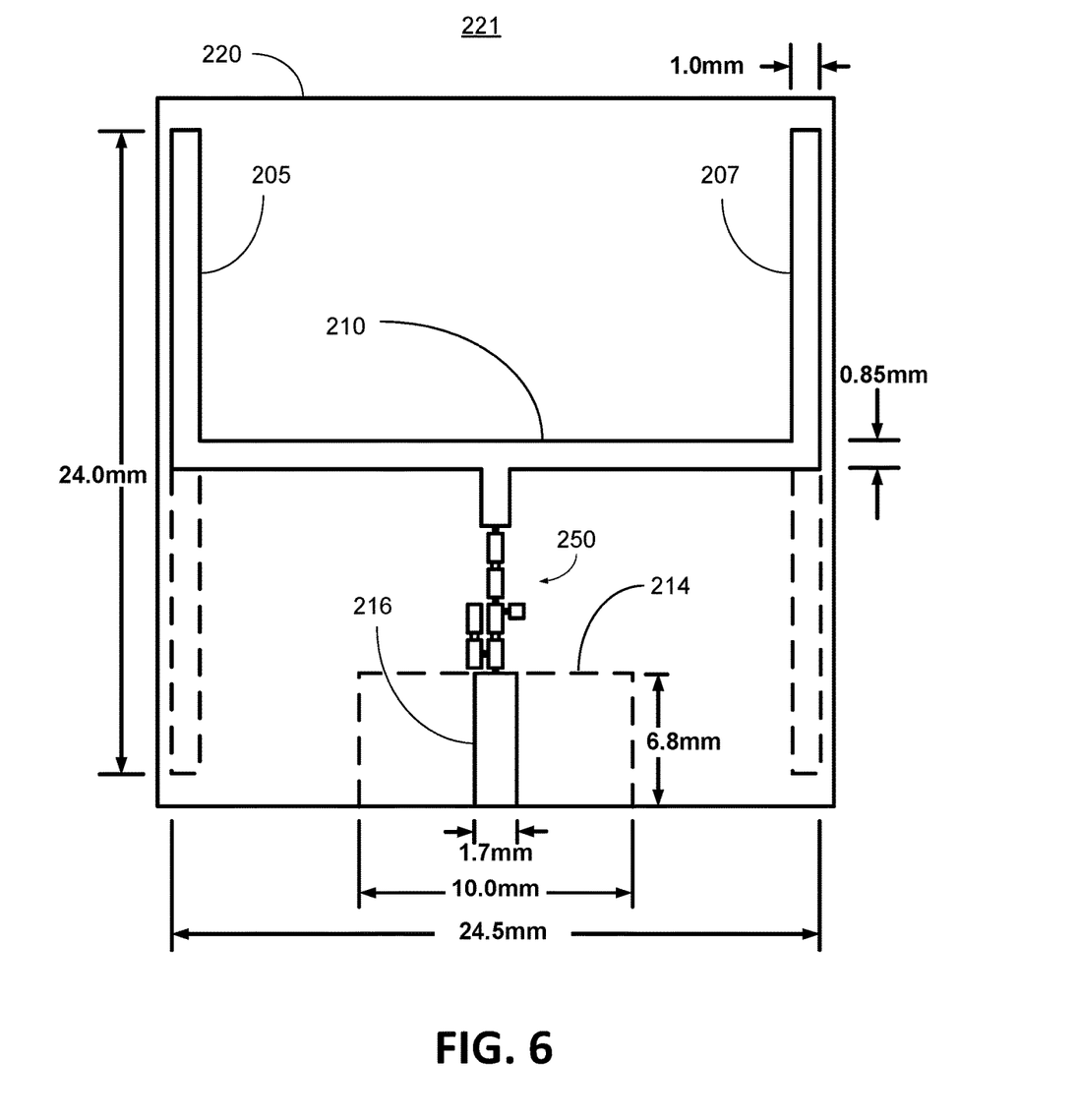
FIG. 6 illustratively depicts dimensions associated with a bolus embodiment consistent with embodiments of the present invention.

As previously mentioned the dielectric spacer 220 separates the microstrip transmission line's ground plane 214 from the microstrip transmission line 216. The microstrip transmission line 216 is on the unbalanced side 402 of the balun circuit 250, accordingly the microstrip transmission line 216 is unbalanced. The first and second parallel plate transmission lines 210 and 212 are balanced 404. As shown in FIG. 6, the microstrip transmission line 216 is 1.7 mm wide and the microstrip transmission line's ground plane 214 is 10 mm wide. Theoretically, the microstrip transmission line's ground plane 214 would extend in every direction infinitely, but in relation to the relatively thin metal microstrip transmission line 216, the microstrip transmission line's ground plane 214 looks essentially infinite. The microstrip transmission line 216 guides a bound electromagnetic wave, which is mostly bound between the microstrip transmission line's ground plane 214 and the microstrip transmission line 216. The bound electromagnetic wave is then transformed by the balun circuit 250 into an electromagnetic wave that travels essentially along the interior sides of the first and second parallel plate transmission lines 210 and 212. Because the first and second parallel plate transmission lines 210 and 212 have opposing fields they act as a transmission line and not radiators. The electromagnetic wave is no longer bound at the dipoles 205 and 207 because the currents are no longer opposing. The dipoles 205 and 207 are radiators. In addition, the currents in the dipoles 205 and 207 and the microstrip transmission line's ground plane 214 extend through the circular ground plate 270 and down the side of the metal cylindrical antenna 290. The waves then radiate essentially omnidirectionally into space via the dipoles 205 and 207 and metal cylinder 290. Hence, the metal cylinder 290 serves as an important part of the overall antenna as shown by the arrows pointing in the same direction. Certain embodiments envision the metal cylinder 290 being a sturdy metal pipe with an added purpose of increasing the density of the entire bolus 100 to target a density of 2.75 g/cc. Additional solid metal slugs (not shown) may be disposed inside the metal cylinder 292 to increase the bolus density to the target density of 2.75 g/cc. The conductive cylindrical antenna 290 can be shortened or lengthened to impact radio wave transmission. The conductive cylindrical antenna 290 can suppress any feedback because it is functioning as a waveguide below cutoff. The conductive cylinder 292 and the slug (not shown) can be electrically connected to the ground terminal of the battery 282 act as an electrical ground path from the negative battery terminal to the conductive cylinder 292 and then to the grounding connections that connect the conductive cylinder 292 to the circular ground plate 270.

Figure 4B:
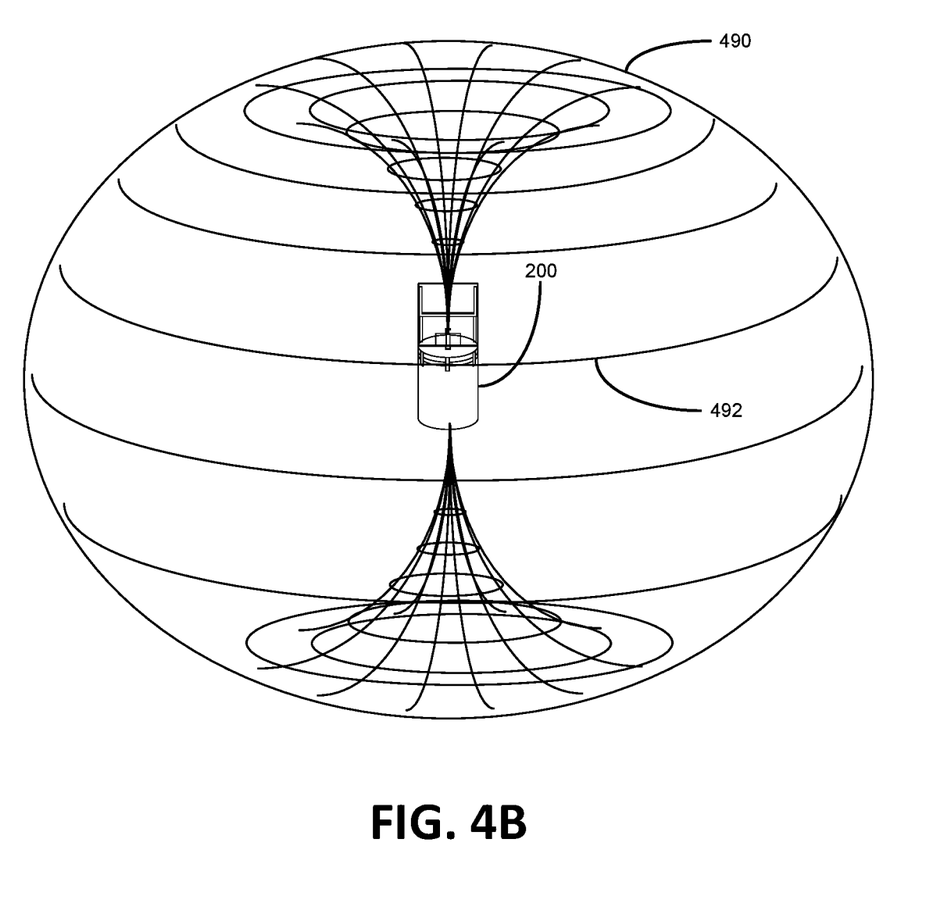
FIG. 4B illustratively depicts a model of the omnidirectional pattern into space generated by the bolus antenna system consistent with embodiments of the present invention.

FIG. 4B illustratively depicts a model of the omnidirectional pattern into space generated by the H-antenna 221 and metal cylinder 290. As is shown, the bolus radiates an omnidirectional RF pattern 490. The radiation lines 492 are used to illustratively show the three-dimensional model of the omnidirectional RF pattern 490. Certain embodiments contemplate the radio frequency at above 800 MHz. Other embodiments envision using non-licensed frequencies, such as 433 MHz and 315 MHz, for example.

With continued reference to FIG. 3, the H-antenna 221 rests atop the circular ground plate 270. The circular ground plate 270, which is the RF ground, produces a continuous ground connection through the ground straps 230 that conduct the electrical currents from the microstrip transmission line 216 generating an extension of electrical currents in the dipoles 205 and 207, thus making the entire length of the bolus 241 (H-antenna 221 and conductive cylinder 223) one complete antenna. Under the circular ground plate 270 is a primary circuit board 276 with a gap 274 separating the primary circuit board 276 from the circular ground plate 270. Certain embodiments envision the gap 274 having a consistent space between the primary circuit board 276 and the circular ground plate 270 created by equal sized spacers (not shown). Other embodiments envision the primary circuit board 276 extending below the circular ground plate and into the conductive cylinder 223. The circular ground plate 270 is electrically connected to the metal cylinder 290 by way of ground straps 230, three of which are shown in this figure. Certain embodiments envision more ground straps or even a continuous ground between the metal cylinder 290 and the circular ground plate 270. Other embodiments envision the ground straps being conductors that may be conductive wire, conductive straps, conductive tape, or other conductive materials that are adhered to the metal cylinder 292 by way of welding, conductive adhesion, or other methods to electrically connect to the metal cylinder 292. Disposed inside of the metal cylinder 290 is a battery 280, which serves as a power supply to the bolus 200. Though not shown, certain embodiments envision filler (potting) material that fills the area around the H-antenna 221 and adds weight to the bolus 100 to help meet the target density of 2.75 g/cc without significant radio energy attenuation.

Figure 5A:
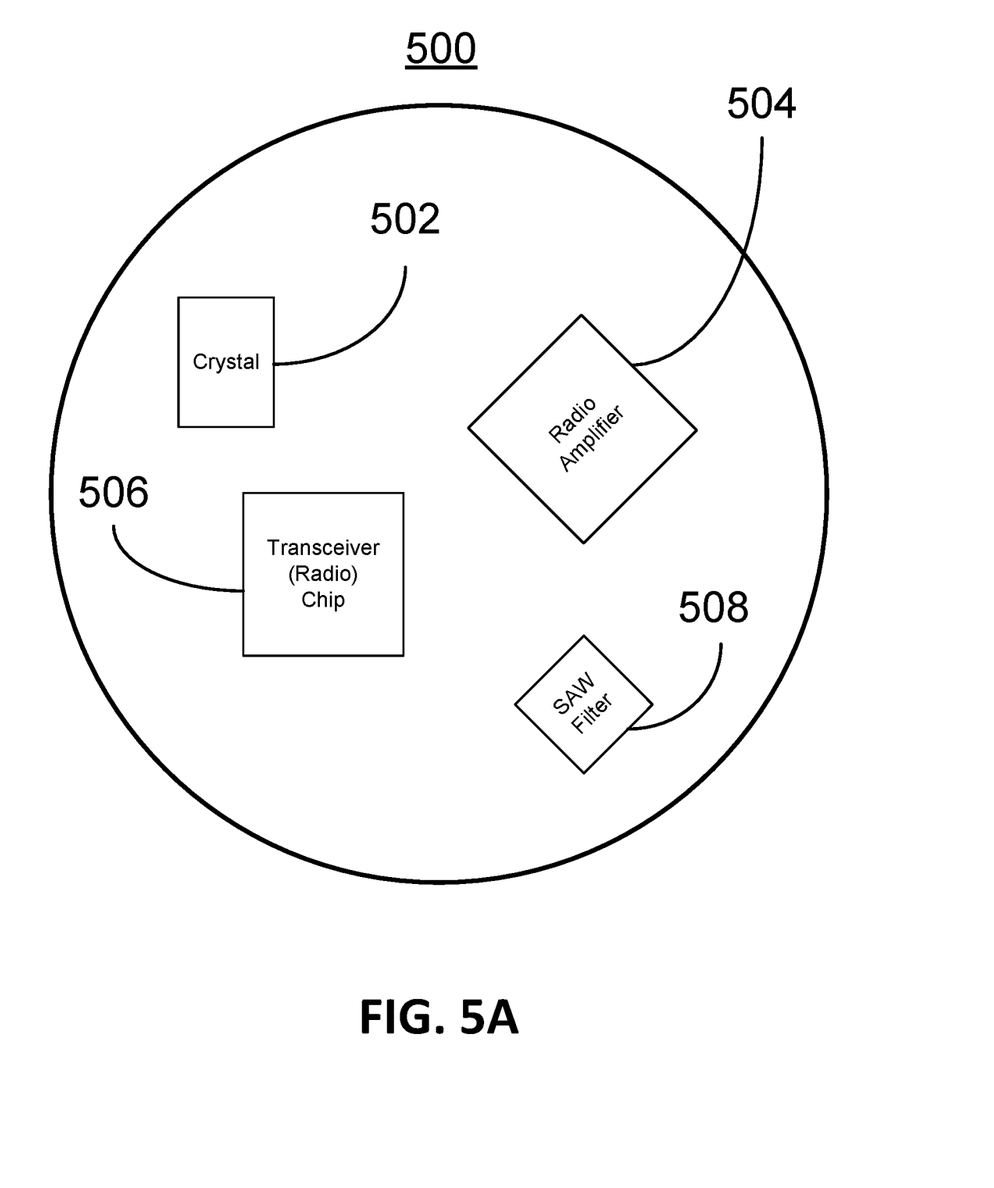
FIGS. 5A and 5B illustratively depict a basic top and bottom circuit board layout embodiment for certain bolus embodiments consistent with embodiments of the present invention.
Figure 5B:
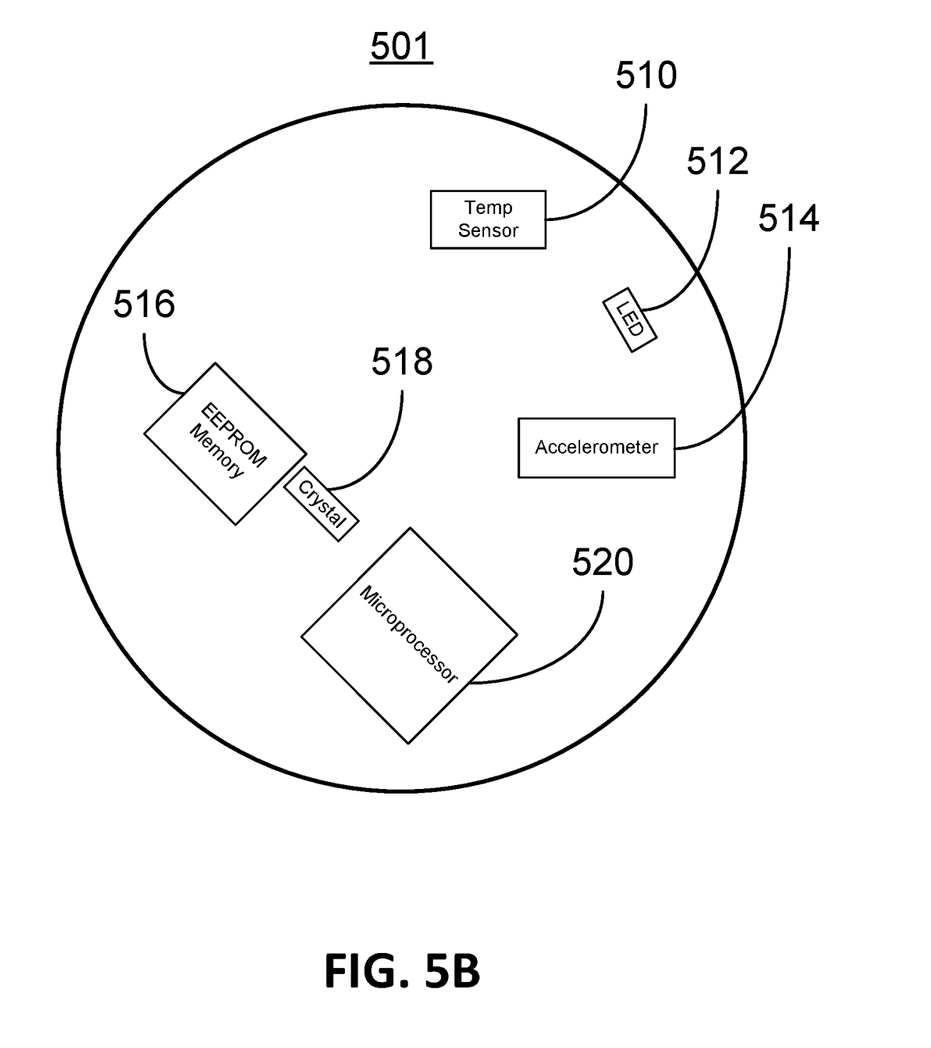

FIG. 5 depicts some examples of the central elements of the circuit board 276 consistent with embodiments of the present invention. The circuit board 276 has a plurality of central elements on a top surface 500 and a bottom surface 501, among standard essential elements such as resisters, capacitors, etc. With reference to the top surface 500, a transceiver chip 506 is directly connect to the microstrip transmission line 216 via the circular ground plate 270, a crystal 502, a radio amplifier 504 and an optional Surface Acoustic Wave (SAW) filter 508. The bottom surface 501 includes a temperature sensor 510 (that can measure the temperature of the cow 102), and accelerometer 514 that senses g-force (e.g., when a cow 102 is lying, eating, drinking or moving around), microprocessor and real time clock 520 (which handles the computing of the bolus 200), memory 516 to store sensor data, received data (such as calving date, illness, treatment, drugs administered, sire, dam, etc.) and retain identification information and an optional LED 512 to indicate that the circuit board 276 is working. The circuit board 276 is powered by the battery 280. The main circuit board 276 fits on top (or inside the) diameter of the metal cylinder 290 of the bolus 200. Though not shown, the circuit board 276 includes a perpendicular "feed" conductors that pass ground to the microstrip transmission line's ground plane 214 and the radio energy from the transceiver chip 506 to the dipoles 205 and 207.

Certain embodiments contemplate the chipset configured with circuitry that balances, or tunes, at least the H-antenna 221 (and in some embodiments the cylindrical antenna as well) to a dielectric constant of cow's tissue, which is similar to saltwater concentrate. In other words, the H-antenna 221 is made to operate over a narrow impedance bandwidth accommodating the dielectric environment of a cow 102. This can be accomplished with integrating passive components to the antenna structure that facilitates near optimal energy transmission from the transmitter to the complex impedance of a cow's stomach. When the antenna 221 and 223 is in free space (in air with a dielectric constant of approximately 1.05), the antenna frequency of operation increases, and in turn produces a large mismatch, which decreases the transmitted power (in some cases by orders of magnitude) and thus reduces intentional and unintentional radiation when the antenna is outside of the cow 102 (or whatever the operating environment for which the antenna 221 and 223 is tuned). For example, with radio waves at a frequency of 915 MHz, blood has an epsilon of 61.3 and sigma is about 1.55. As is known to those skilled in the art, epsilon is the relative dielectric permittivity value, which is sometimes called the dielectric constant. Sigma is the conductivity. Certain embodiments contemplate the circuitry used for tuning the antennas being static, which is defined as circuitry that cannot be adjusted. While other embodiments contemplate dynamic circuitry that can be changed to alter the tuning of at least the H-antenna 221 depending on the condition with which it is confronted. In certain embodiments, the bolus 200 is tuned to radiate radiofrequency waves near optimal efficiency when passing through about 200 mm of cow before transmitting through air. This is about the thickness between where the bolus 100 sits in a cow's stomach and outside the cow 102. The antenna system, the H-antenna 221 and the conductive (metal) cylindrical antenna 223, can be tuned so that when outside of the cow 102 (before the bolus is disposed in a cow's stomach) the antenna system performs very poorly and limits the radiated radio power when not in the cow. In other words, the antenna only works well when the radio waves first pass through about 100 mm of cow before continuing to transmit through air. This is an important feature to avoid conflicting signals regulated by the Federal Aviation Administration (FAA) and other regulatory agencies.

FIG. 6 depicts dimensions of an embodiment of the H-antenna 221 consistent with embodiments of the present invention. In this embodiment, the electrically small H-antenna 221 possesses a first dipole 205 having an overall length of 24 mm and width of 1 mm and a second dipole 207 having a length of 24 mm and a width of 1 mm. The first parallel plate transmission line 210 has a width of 0.85 mm and an overall length of 24.5 mm. The microstrip transmission line 216 has a height of 6.8 mm and the width of 1.7 mm. The microstrip transmission line's ground plane 214 has a height of 6.8 mm and a width of 10 mm.

Figure 7:
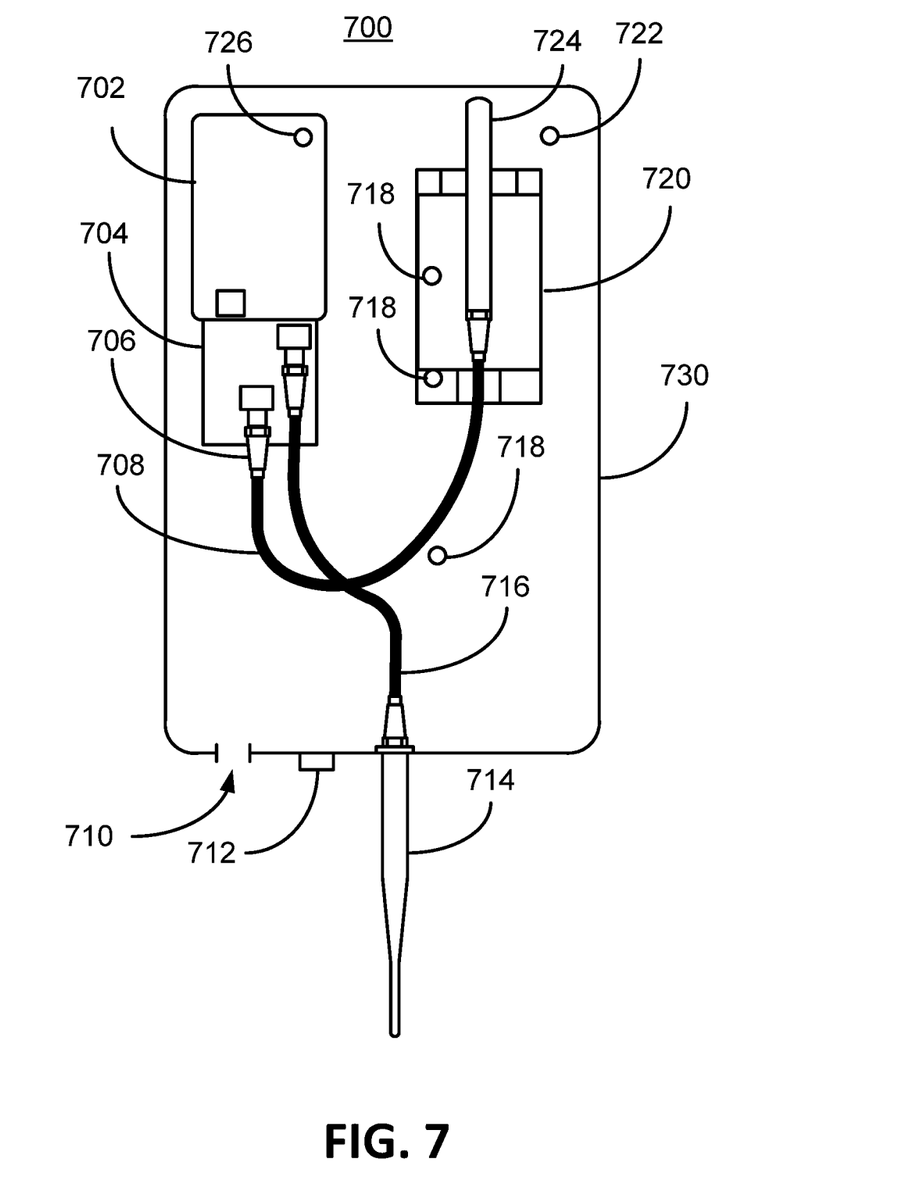
FIG. 7 depicts an embodiment of an external transceiver system in accordance with embodiments of the present invention.

FIG. 7 depicts an embodiment of an external transceiver system 700, which acts as a gateway between signals from the cow bolus 100 and data transmitted to a computing system (not shown) consistent with embodiments of the present invention. The external transceiver system 700 is configured for two-way communication with one or more boluses 100. Embodiments of the external transceiver enclosure 730 can include an enclosure that is suitable for mounting inside of a building and may be waterproof to withstand the elements outdoors. The external transceiver system 700 generally includes radio transceiver electronics, nonvolatile memory, microprocessor, real-time clock, connection to a single board computer, and other supporting circuitry. More specifically, the single board computer 702 serves as an interface between the main external transceiver system circuit board 704 (which can include in microprocessor and nonvolatile memory) and a client or host computer (not shown). The non-volatile memory can be used to store data received from the bolus 100 until the successfully passed to a host computer (not shown). The single board computer 702 facilitates data processing at the external transceiver system 700 in addition to a wide range of data formatting and physical layer data transfer, such as ethernet, cellular modem, long-range Wi-Fi interface, RS-232, laser data link, etc. The single board computer 702 is connected to the main external transceiver system circuit board 704. The single board computer 702 can have other features associated with it including a board power On LED 726. The single board computer 702 can also be used for data processing raw data received from the bolus 100 and other separated data collection/processing devices (e.g., tank level monitors, weather stations, video cameras) before processing and/or transmitting to a host computer (not shown). Moreover, the single board computer 702 can reformat data received from the bolus 100 and send it over a wide variety of interfaces (such as Ethernet, cellular modem, RS-232, long-range Wi-Fi, and others) to a host computer. Optionally connected to the single board computer 702 is a radio re-transmitter module (such as a long-range Wi-Fi transmitter module) configured to pass data collected by the external transceiver system 700 to a data collection center. This has additional benefits when the external transceiver system 700 is remotely deployed. Radio re-transmitter is connected to a Wi-Fi antenna 724 via a coaxial cable 708. Cables 708 and 716 are connected to various components via cable connectors 706. A drain/vent 710 can be located on a bottom side of the external transceiver system 700, which can be especially useful if located outside. Other elements can include a power switch 712, various status programmable LEDs, power On LED 722, for example. The external transceiver system 700 requires a power supply/source such as a battery, direct power line, solar, just to name several examples. In the present embodiment a solar DC power supply controller 720 is shown. The external transceiver system 700 can transmit and receive signals to and from a bolus 100 via the bolus radio link antenna 714, which is connected to the main external transceiver system circuit board 704. Certain embodiments envision the bolus radio link antenna 714 configured for receiving 915 MHz signals. Other embodiments contemplate the bolus 100 communicating with the external transceiver system 700 at a frequency above 800 MHz.

Certain embodiments of the present invention contemplate a bolus 100 for monitoring physiological data of a ruminant animal where the bolus 100 is administered to the animal down its esophagus. As previously mentioned, the density and size of the bolus 100 causes it to become trapped in one of the animal stomachs. The bolus 200 includes a microprocessor, memory, a resettable real-time electronic clock, bolus firmware that controls taking data from sensors integrated in the bolus 200, and a two-way radio transceiver that can send and receive data through the cow 102 and to a receiver station 106. The radio in the bolus 100 can be set to transmit at regular time intervals. Certain embodiments envision the receiver station 106 (or external transceiver) sending an acknowledgment message and an accrual age time and date message back to the bolus 100 when data has successfully been received at the receiver station. In this scenario, when the bolus 100 does not receive an acknowledgment from the receiver station, all data in the bolus 100 is stored in memory in the bolus within an accrual timestamp. At the next preset interval, all data in memory is transmitted. If acknowledgment is received by the receiver station 106, then the stored memory is cleared. If the acknowledgment is not received, then the latest timestamp reading is added to memory with a timestamp. The two-way communication also allows an end-user or host computer system to send a message to the bolus 100 (with the acknowledgment message) to do the following functions: change the transmit interval, change center reading interval (which may be different from the radio transmit interval), update the bolus firmware (adding new functionality to the bolus firmware), or turn on or off different sensors or functions in the bolus 100. To save battery power and to keep the radio channel clear, no data that has previously been successfully sent and acknowledged will be sent again.

Other embodiments contemplate the firmware controlling the bolus 100 can be programmed or updated where the taking of sensor data or the transmission interval is dynamic based on the sensor data. For example, instead of transmitting temperature and accelerometer data every one hour, sample the temperature and accelerometer data every 5 minutes and immediately transmit that data if the temperature is above 102° F. and/or if the accelerometer data is above 1 point 5 G's.

Yet other embodiments contemplate and accelerometer that can monitor the movement of the animal and the orientation of the bolus 100 and sudden jumps in g-force using sensors sampling methods that can be set and reset by the end-user by way of the two-way radio communication. The sensor can also be dynamically set by programmable logic in the bolus 100 that can be updated by two-way radio. For example, the bolus firmware can be set to sample the g-force of the accelerometer every 15 minutes for 15 seconds at high sampling rate of 10 times per second if the temperature of the animal is at least 1° F. above baseline temperature.

Certain embodiments contemplate the two-way radio connection use to command the bolus 100 to go from low-power radio transmissions while outside of the cow 102 to high power transmissions after certain amount of time has elapsed when the bolus 100 is implanted in the cow 102. This can be beneficial when the bolus operates in non-licensed frequency bands above 850 MHz.

Other embodiments contemplate an end-user or computer system using the two-way radio system to set or reset a sensor "alert" parameter (or logical condition using multiple sensors) that will change the bolus sensor sampling interval, or sensor transmit interval, or bolus on-board edge-computing data analysis. This can be furthered whereby the bolus data can be time stamped in the bolus 100, such that sensor sampling intervals can be changed to maintain a time synchronization that is not otherwise possible without on-board bolus time stamping.

It is envisioned that if a low-cost real-time clock is created inside of the microprocessor using its relatively low accuracy real-time clock functionality, the microprocessor real-time clock can be kept from drifting and becoming inaccurate by continually resetting the time within "accurate time" that is sent with each acknowledgment of receipt data from the receiver station 106.

Embodiments envision battery preservation whereby the bolus 100 consumes ultralow power when not sampling sensors or transmitting using the radio transceiver. This can facilitate extended life with no need to turn off the bolus 100 before administering the bolus 100 to the animal. When in this quiescent state (sleep state), the microprocessor disconnects all circuitry from the battery power source except power to the microprocessor. The microprocessor is then put in a "deep sleep" so that all microprocessor functionality is turned off except the necessary internal circuits to wake up the bolus 100 to take sensor readings at the reprogrammable interval or at a sensor event.

It is contemplated that the two-way communication from the bolus 100 to the external transceiver station 106 can be used to write calibration coefficient data to the bolus 100 that can be utilized by an onboard bolus algorithm to adjust sensor readings to calibrated standards providing higher accuracy sensor readings. The sensor readings as well as other data transmitted by the bolus 100 can be passed to a host computer (not shown).

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though a battery is used herein as a power source, some other embodiments contemplate a passive RFID bolus system that is powered/energized when in a high-energy interrogation zone while still maintaining substantially the same functionality without departing from the scope and spirit of the present invention. Another example can include using the electrically small antenna design for the bolus in a tank of salt water or some other medium with a different dielectric than air. Yet another example can include placing a plurality of different sensors on the exterior surface of the bolus to measure and/or sense chemicals with which the bolus may come into contact and feeding all sensed results/values to the electronics (including memory) within the bolus while staying within the scope and spirit of the present invention. Further, the terms "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed.

What is claimed is:

1. A bolus comprising:
   an electrically small H-antenna extending from a front side of a ground plate, said H-antenna electrically connected to a power supply and a signal transmitter by way of a microstrip transmission line, the microstrip transmission line opposing a ground plane that is at least three times greater width than said microstrip transmission line and separated from said microstrip transmission line by a dielectric spacer, said H-antenna comprising two parallel dipoles and a two parallel plate transmission lines;
   a conductive cylindrical antenna extending from a backside of said ground plate and electrically connected to said ground plate, said metal cylindrical essentially housing said power supply;
   said bolus configured to radiate essentially omnidirectional electromagnetic waves generated by electrical currents aligned and in a common direction in both said parallel dipoles and said conductive cylindrical antenna when powered by said signal transmitter.

2. The bolus of claim 1 further comprising a capsule that encapsulates and hermetically seals said electrically small H-antenna, said signal transmitter, said ground plate, the dielectric spacer, said microstrip, and said conductive cylindrical antenna.

3. The bolus of claim 1 wherein said bolus is weighted to stay retained in a stomach of a ruminant animal throughout the life of said ruminant animal.

4. The bolus of claim 1 wherein said to parallel plate transmission lines possess opposite electrical currents that cancel each other out when said signal transmitter provides power to said antenna.

5. The bolus of claim 1 wherein said omnidirectional electromagnetic waves are significantly attenuated when said bolus is in operation outside of a ruminant animal compared to being in said ruminant animal.

6. The bolus of claim 5 wherein said signal transmitter is comprised by a printed circuit board that possesses static circuits that tune the H-antenna to transmit said electromagnetic waves significantly further when said bolus is inside of said ruminant animal as compared to outside of said ruminant animal.

7. The bolus of claim 1 further comprising a printed circuit board that is shielded from said electrical currents by said conductive cylindrical antenna.

8. The bolus of claim 1 wherein said dipoles of the H-antenna are spaced apart approximately the same distance as the diameter of said metal cylindrical antenna.

9. The bolus of claim 1 configured for two-way communication using radio frequency with an external transceiver.

10. The bolus of claim 1 further comprising a unique identification and at least one sensor adapted to measure a physical parameter associated with a host ruminant animal, said unique identification and at least one value associated with said physical parameter adapted to be transmitted by said omnidirectional magnetic waves.

11. A bolus comprising:
    an electrically small H-antenna extending from a conductive cylindrical antenna;
    a ground plate interposed between said H-antenna and said conductive cylindrical antenna, said H-antenna connected to said conductive cylindrical antenna;
    a battery disposed inside of said conductive cylindrical antenna; and
    a signal transmitter configured to generate electrical currents that essentially align in one direction in both said H-antenna and said conductive cylindrical antenna, said H-antenna and said conductive cylindrical antenna are adapted to generate radiofrequency waves from said electrical currents.

12. The bolus of claim 11 wherein said bolus is weighted to remain inside of a ruminant animal's stomach until the ruminant animal is no longer living.

13. The bolus of claim 11 further comprising a unique identification and at least one sensor adapted to measure a physical parameter associated with a host ruminant animal, said unique identification and at least one value associated with said physical parameter adapted to be transmitted by said radiofrequency waves.

14. The bolus of claim 13 wherein said radiofrequency waves are essentially omnidirectional.

15. The bolus of claim 11 wherein said bolus possesses circuitry that is configured to tune at least said H-antenna to transmit said radiofrequency waves more powerfully when said bolus is disposed in a ruminant animal than when said bolus is located outside of said ruminant animal.

16. A method comprising:
    providing a bolus possessing an electrically small H-antenna and a conductive cylindrical antenna, the H-antenna possessing two parallel dipoles that are in line with the outer surface of the conductive cylindrical antenna;
    energizing the H-antenna and the conductive cylindrical antenna with a battery contained in said conductive cylindrical antenna via a signal transmitter to generate electrical currents that are essentially pointed in the same direction along said dipoles and the outer surface of said conductive cylindrical antenna;
    transmitting at least identification of said bolus via a radio signal wave generated by said electrical currents in said dipoles and said outer surface of said conductive cylindrical antenna.

17. The method of claim 16 further comprising alternating the electrical currents at a frequency over 800 MHz.

18. The method of claim 16 further comprising generating essentially omnidirectional radio waves via the H-antenna and the conductive cylindrical antenna.

19. The method of claim 16 wherein radio wave transmitted by said bolus are significantly weaker when said bolus is transmitting signals outside of a ruminant animal than when said bolus is transmitting signals inside of said ruminant animal.

20. The method of claim 16 further comprising obtaining at least one sensor value from a sensor within said bolus and transmitting said at least one sensor value via said radio signal wave to an external receiving device.

\* \* \* \* \*